(12) United States Patent
Wang et al.

(10) Patent No.: US 9,364,635 B2
(45) Date of Patent: Jun. 14, 2016

(54) COMPUTER CONTROLLED STEERABLE TIP GUIDE CATHETER

(71) Applicant: Covidien LP, Mansfield, MA (US)

(72) Inventors: Edwin Wang, Tustin, CA (US); Christopher Folk, Los Angeles, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/032,255

(22) Filed: Sep. 20, 2013

(65) Prior Publication Data

US 2015/0088060 A1 Mar. 26, 2015

(51) Int. Cl.
| | | |
|---|---|---|
| *A61M 25/01* | (2006.01) | |
| *G06F 19/00* | (2011.01) | |
| *A61M 25/09* | (2006.01) | |
| *A61M 25/00* | (2006.01) | |
| *A61B 17/00* | (2006.01) | |

(52) U.S. Cl.
CPC ....... *A61M 25/0105* (2013.01); *A61M 25/0158* (2013.01); *G06F 19/3406* (2013.01); *A61B 2017/00203* (2013.01); *A61M 2025/0058* (2013.01); *A61M 2025/09133* (2013.01)

(58) Field of Classification Search
CPC ................. A61M 2025/0058; A61M 25/0158; A61M 25/0105; A61M 2025/0915; A61M 25/0053; A61M 25/0054; A61M 25/0141; A61M 25/0144; G06F 19/3406; G06F 19/3437; G06F 3/017
USPC ......... 604/528, 525, 95.01, 95.04, 510, 95.05
See application file for complete search history.

(56) References Cited

U.S. PATENT DOCUMENTS

| | | | | |
|---|---|---|---|---|
| 5,644,613 | A | * 7/1997 | Mick .................. | A61B 6/12 348/E5.088 |
| 6,463,361 | B1 | * 10/2002 | Wang et al. ................ | 700/258 |
| 6,679,836 | B2 | 1/2004 | Couvillon, Jr. | |
| 6,835,173 | B2 | * 12/2004 | Couvillon, Jr. .......... | 600/146 |
| 6,965,812 | B2 | 11/2005 | Wang et al. | |
| 6,997,870 | B2 | * 2/2006 | Couvillon, Jr. .......... | 600/146 |

(Continued)

FOREIGN PATENT DOCUMENTS

WO 2011123669 A1 10/2011

OTHER PUBLICATIONS

International Search Report and Written Opinion from counterpart International Patent Application No. PCT/US2014/054486, mailed Dec. 11, 2014, 11 pp.

(Continued)

*Primary Examiner* — Kevin C Sirmons
*Assistant Examiner* — William Carpenter
(74) *Attorney, Agent, or Firm* — Elizabeth A. O'Brien, Esq.

(57) ABSTRACT

A catheter system is provided. The system includes a catheter having an elongated flexible body and one or more electroactive polymer actuators disposed along the elongated flexible body. The electroactive polymer actuators are adapted to cause a change in configuration of the elongated flexible body. The system also includes a controller adapted to transmit the control signal to the electroactive polymer actuators. The controller includes a memory storing a plurality of control signals corresponding to a plurality of predetermined configurations of the catheter and a user-interface coupled to the memory. The user-interface is configured to select one or more configurations from the plurality of predetermined configurations in response to user input.

22 Claims, 4 Drawing Sheets

(56) References Cited

U.S. PATENT DOCUMENTS

| | | |
|---|---|---|
| 7,766,896 B2 | 8/2010 | Kornkven Volk et al. |
| 8,209,195 B2 | 6/2012 | Dicks et al. |
| 8,671,817 B1* | 3/2014 | Bogusky ............... 87/35 |
| 2002/0137014 A1* | 9/2002 | Anderson ........... A61F 2/07 434/262 |
| 2003/0236445 A1* | 12/2003 | Couvillon, Jr. ............ 600/114 |
| 2004/0143160 A1* | 7/2004 | Couvillon, Jr. ... A61M 25/0105 600/114 |
| 2004/0254566 A1* | 12/2004 | Plicchi et al. ............... 606/1 |
| 2007/0123750 A1* | 5/2007 | Baumgartner ....... A61B 1/0058 600/143 |
| 2009/0024086 A1* | 1/2009 | Zhang et al. ............. 604/95.05 |
| 2011/0270126 A1 | 11/2011 | Gunday et al. |
| 2012/0173217 A1* | 7/2012 | Heimbecher ....... G06F 19/3437 703/7 |
| 2012/0239032 A1 | 9/2012 | Zhang et al. |
| 2013/0123692 A1* | 5/2013 | Zhang et al. ............. 604/95.05 |

OTHER PUBLICATIONS

International Preliminary Report on Patentability from International Application No. PCT/US2014/054486, mailed Mar. 31, 2016, 8 pp.

* cited by examiner

COMPUTER CONTROLLED STEERABLE TIP GUIDE CATHETER

BACKGROUND

1. Technical Field

The present disclosure generally relates to medical systems and methods, and, in particular, relates to systems and associated methods for controlling guide catheters, and more particularly to guide catheters whose shape, configuration, and/or stiffness can be tailored to a patient through programmed control.

2. Description of Related Art

Catheters are used routinely in medical procedures, including coronary, neural, cardiac and other vascular procedures. In particular, a guide catheter is inserted initially and provides a channel through which suitable interventional devices, such as angioplasty devices, peripheral or neurovascular stent delivery catheters, electrophysiology catheters, metallic coils can be introduced. Catheters also permit delivery of bioactive agents, such as embolization materials, anti-inflammatory agents, contrast agents, and the like.

In use, the guide catheters are typically advanced into the patient's vasculature, commonly over a guidewire, to a desired treatment location such as in the neurovasculature, where its tip is placed against or otherwise near the region to be treated.

Although guide catheters are available in a variety of preformed sizes and shapes, conventional guide catheters may be difficult to steer and advance through extremely tortuous vasculature such as that found in the neurovasculature. Accordingly, there is a need for guide catheters that may be shaped into any suitable configuration.

SUMMARY

According to an embodiment of the present disclosure, a catheter system is provided. The system includes a catheter having an elongated flexible body and one or more electroactive polymer actuators disposed along the elongated flexible body. The electroactive polymer actuators are adapted to cause a change in configuration of the elongated flexible body. The system also includes a controller adapted to transmit a control signal to the electroactive polymer actuators. The controller includes a memory storing a plurality of control signals corresponding to a plurality of predetermined configurations of the catheter and a user-interface coupled to the memory. The user-interface is configured to select one or more configurations from the plurality of predetermined configurations in response to user input.

According to one aspect, the user-interface includes a voice control module. The voice control module may include a microphone and a speech-recognition engine. The speech-recognition engine may be configured to detect voice input and to match the voice input to one or more commands associated with the configuration. The commands may be associated with the change in the configuration of the elongated flexible body and may be selected from the group consisting of deflection, direction, orientation, and combinations thereof. The commands may correspond to an anatomical structure and the configuration may correspond to a shape of the catheter for conforming to the anatomical structure.

According to an embodiment of the present disclosure, a method for controlling a catheter for accessing a body lumen is provided. The method includes providing a user input for controlling a catheter to a controller where the catheter has an elongated flexible body and one or more electroactive polymer actuators disposed along the elongated flexible body, selecting one or more configurations for the catheter from a plurality of predetermined configurations in response to the user input and transmitting the control signal to the electroactive polymer actuators to cause a change in configuration of the elongated flexible body in response thereto. The user input may be a voice input.

According to another aspect, the method further includes detecting the voice input and matching the voice input to the command associated with the configuration. The command may be associated with the change in the configuration of the elongated flexible body and may be selected from the group consisting of deflection, direction, orientation, and combinations thereof. The command may correspond to an anatomical structure and the configuration may correspond to a shape of the catheter for conforming to the anatomical structure.

According to an embodiment of the present disclosure, a system for controlling a catheter for accessing a body lumen is provided. The system includes a computer processor that is operable to execute a computer program product tangibly embodied in a computer-readable storage medium. The computer program product is operable to cause the computer processor to: receive a user input for controlling a catheter having an elongated flexible body and one or more electroactive polymer actuators disposed along the elongated flexible body; select one or more configurations for the catheter from a plurality of predetermined configurations in response to the user input; and transmit the control signal to the electroactive polymer actuators to cause a change in configuration of the elongated flexible body in response thereto.

According to one aspect, the system further includes a memory coupled to the computer processor storing a plurality of control signals corresponding to the plurality of predetermined configurations of the catheter and a user-interface coupled to the memory and configured to select the configuration from the plurality of predetermined configurations in response to user input. The user-interface may include a voice control module. The voice control module may include a microphone and a speech-recognition engine. The speech-recognition engine may be configured to detect voice input and to match the voice input to at least one command associated with the at least one configuration. The command may be associated with the change in the configuration of the elongated flexible body and may be selected from the group consisting of deflection, direction, orientation, and combinations thereof. The command may also correspond to an anatomical structure and the configuration may correspond to a shape of the catheter for conforming to the anatomical structure.

The systems and methods for controlling a catheter according to the present disclosure allow for more precise control than conventional catheter control mechanisms by providing preprogrammed configurations for the catheter that are linked to specific anatomical structures, which are associated with predetermined voice input commands. In particular, the present disclosure allows a clinician to remotely control relatively long catheters such as those from about 90 centimeters to about 180 centimeters catheter using hands-free, e.g., voice, input, while guiding catheter into tortuous vasculature, e.g., neurovasculature. Other aspects, features and/or benefits will be apparent from the description, the drawings and the claims.

BRIEF DESCRIPTION OF THE DRAWINGS

Embodiments of the present disclosure will be readily appreciated by reference to the drawings wherein.

DESCRIPTION

In the following description, the terms "proximal" and "distal" as used herein refer to the relative position of the system in a body lumen such as a blood vessel, e.g., in the neurovascular region. The "proximal" or "trailing" end of the system is the portion that is closest to the clinician. The "distal" or "leading" end of the system is the portion that is placed farthest into a body lumen from the entrance site.

The methods and systems of the present disclosure have particular application in neurovascular procedures, but may be used in any interventional, diagnostic, and/or therapeutic procedure including coronary vascular peripheral vascular, and gastro-intestinal applications in addition to a neurovascular application.

As used herein, the term "catheter" is used to mean any intravascular or non-intravascular catheter including, but not limited to, microcatheters, diagnostic catheters, guide catheters, atherectomy catheters, stent delivery catheters, and combinations thereof. In the figures below, the full length of the catheter of the disclosed system is not shown. The length and diameter of the catheter may vary depending on the particular application. In a neurovascular application, the length may range from about 90 centimeters to about 180 centimeters, and the inner diameter of the catheter may range from about 0.0165 inches to about 0.027 inches. Other dimensions are also contemplated.

The various embodiments of the disclosure are described below in connection with the figures. It should be understood that for purposes of better describing the disclosure, the figures may not be to scale. Further, some of the figures may show enlarged or distorted portions to illustrate features that would not otherwise be apparent. In the figures, like numerals also represent similar elements across multiple figures and/or embodiments.

Figure 1:
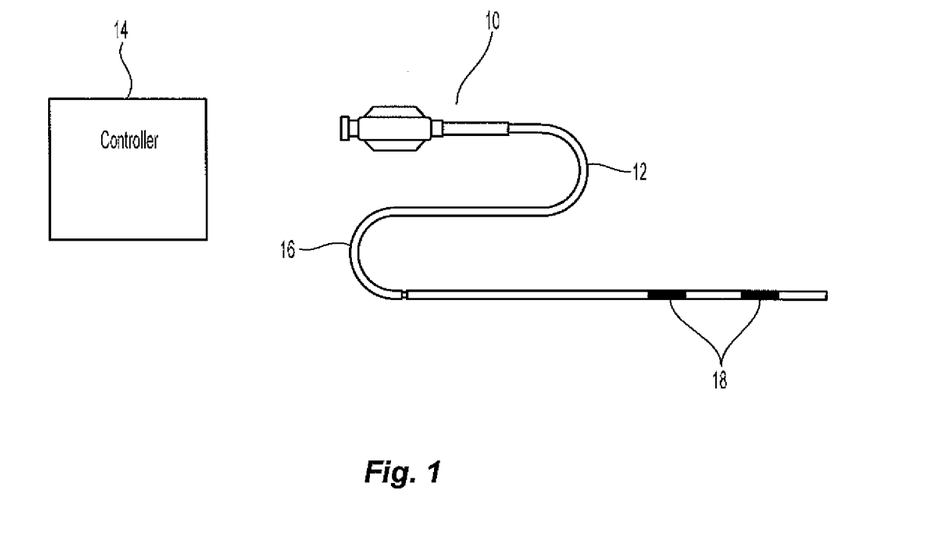
FIG. 1 is a perspective view of a system for controlling an intravascular catheter including an electroactive polymer actuator in accordance with the principles of the present disclosure.
Figure 2:
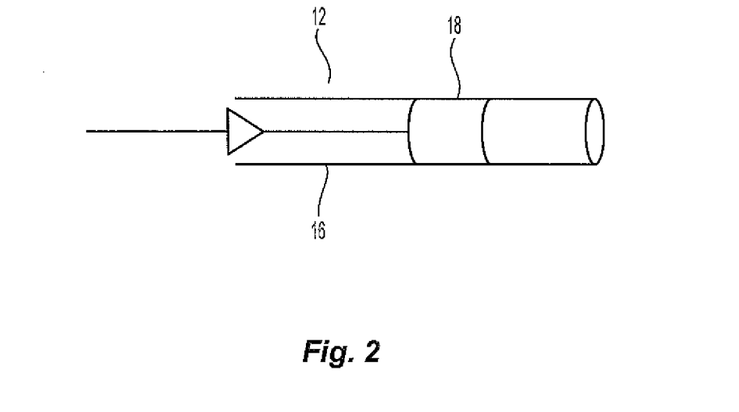
FIG. 2 is a side view of the catheter of FIG. 1 in a first configuration with the electroactive polymer actuator in an unactuated state in accordance with the principles of the present disclosure.
Figure 3:
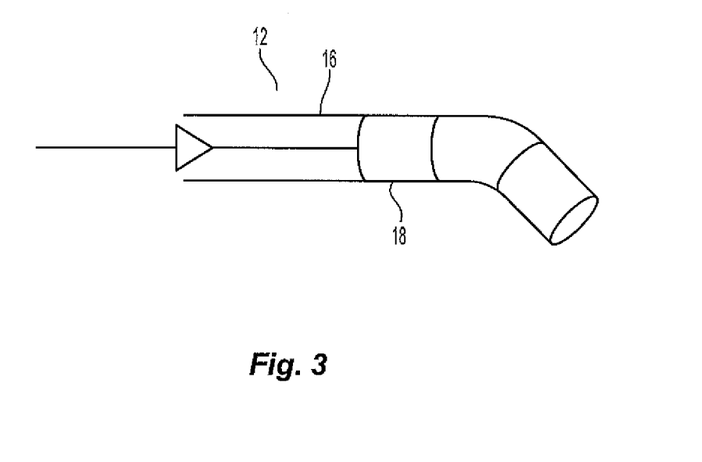
FIG. 3 is a side view of the catheter of FIG. 1 in a second configuration with the electroactive polymer actuator in an actuated state in accordance with the principles of the present disclosure.

In FIG. 1, a system 10 of the present disclosure is illustrated and includes a catheter 12 coupled to a controller 14 configured to adjust configuration of the catheter 12. With reference to FIGS. 1-4, catheter 12 of the disclosed system includes an elongated flexible body 16 and one or more electroactive polymer ("EAP") actuators 18 disposed along a portion of or the entire length thereof. The controller 14 is configured to control the configuration of the catheter 12 by transmitting control signals to the EAP actuator 18. FIG. 2 shows the catheter 12 in a first configuration, in which the EAP actuator 18 is not energized and the flexible body 16 of the catheter 12 is not modified. Once the EAP actuator 18 is energized by the controller 14, the EAP actuator 18 deflects the flexible body 16 of the catheter 12 as shown in FIG. 3.

In embodiments, the catheter 12 may include multiple EAP actuators 18 disposed along its body allowing for deflection of the catheter 12 along multiple points as shown in FIG. 1. In further embodiments, multiple EAP actuators 18 may be actuated sequentially to contract and expand thereby moving the catheter 12 longitudinally (e.g., withdrawing or advancing) within a blood vessel.

The degree of deflection of the flexible body 16 may be controlled by adjusting the amplitude of a control signal supplied to the EAP actuator 18 by the controller 14. In embodiments, where multiple EAP actuators 18 are disposed on the flexible body 16 each of the EAP actuators 18 may be energized by independent control signals to provide for tortuous configuration of the catheter 12.

Figure 4:
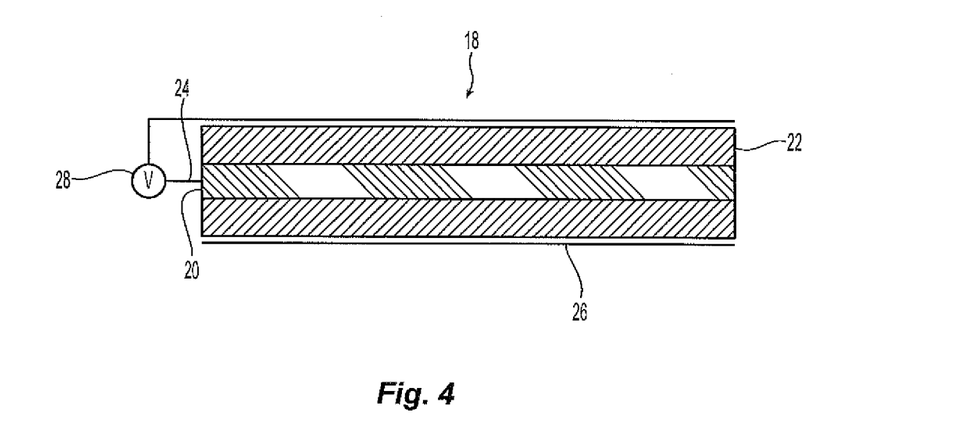
FIG. 4 is a side, cross-sectional, schematic view of the electroactive polymer actuator of the catheter of FIG. 1 in accordance with the principles of the present disclosure.

FIG. 4 shows a cross-sectional, schematic view of the EAP actuator 18. The EAP actuator 18 may include one or more rings, sheaths, fibers, and any other suitable structures formed from an electroactive polymer. In embodiments, the EAP actuator 18 may include multiple filaments or layers of EAP material 20 (FIG. 4). Each filament or layer is electrically isolated from the neighboring filaments or layers and includes an electrically conductive electrode on its outer surface or embedded therein.

The EAP material 20 may be any suitable polymer characterized by its ability to change shape in response to electrical stimulation. Suitable electroactive polymers include, but are not limited to, polyaniline, polysulfone, polypyrrole, polyacetylene, and combinations thereof. In embodiments, the EAP material 20 may be biocompatible since the EAP material 20 may contact the patient during use. These polymers may include a conjugated backbone and may become more electrically conductive under oxidation or reduction. In particular, oxidation or reduction leads to a charge imbalance that, in turn, results in a flow of ions into the EAP material 20.

With continued reference to FIG. 4, the EAP material 20 is in contact with an electrolyte 22, which supplies a flow of ions through the EAP material 20. The ions act as dopants, which enter the EAP material 20. Transfer of ions, in turn results in dimensional changes, such as expansion or contraction due to ion insertion between polymer chains and/or inter-chain repulsion.

The electrolyte 22 may contact a portion or the entire surface of the EAP material 20. The electrolyte 22 may be any conductive material that provides for ion migration and may be a liquid, a gel, a solid, and combinations thereof. In embodiments, in which the electrolyte 22 is a solid, the electrolyte 22 is configured to move along with the EAP material 20 to maintain contact and to avoid delamination therebetween. In embodiments, in which the electrolyte 22 is a gel, the electrolyte 22 may be an agar or polymethylmethacrylate (PMMA) gel and may optionally contain a salt or any other suitable dopant. In embodiments, in which the electrolyte 22 is a liquid, the electrolyte 22 may be a buffer solution including any suitable ions, such as sodium, chloride, phosphate, and the like.

The EAP actuator 18 also includes an active electrode 24 coupled to the EAP material 20 and a return electrode 26 coupled to the electrolyte 22. The active and return electrodes 24, 26 may be any electrical conductors including, but not limited to, a conductive polymer, a conducting polymer gel, a metal, such as gold or platinum, which may be formed by electroplating, chemical deposition, printing, and combinations thereof. The active and return electrodes 24, 26 are coupled to an energy source 28 controlled by the controller 14, which when energized results in migration of ions through the EAP material 20, thereby contracting and/or expanding EAP material 20. Dimensional changes in the EAP material 20 modify the direction of the EAP actuator 18, thereby flexing the flexible body 16 of the catheter 12. In particular, as shown in FIG. 2, when the active and return electrodes 24, 26 are not energized, the EAP actuator 18 does not affect the configuration of the flexible body 16 of the catheter 12. As shown in FIG. 3, when the active and return electrodes 24, 26 are energized, the EAP actuator 18 deflects the flexible body 16 of the catheter 12.

Figure 5:
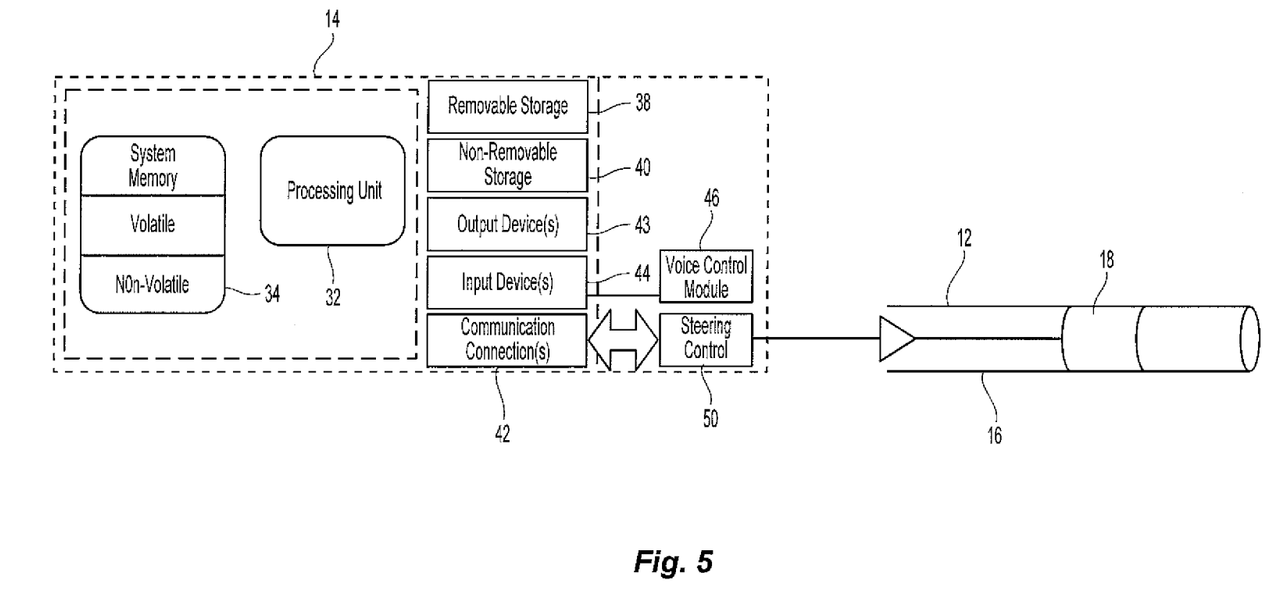
FIG. 5 is a block diagram of a controller of the system of FIG. 1 in accordance with the principles of the present disclosure.

With reference to FIGS. 1 and 5, the controller 14 is configured to supply one or more control signals to the EAP actuators 18 to modify the configuration of the catheter 12, which may include adjustments to the deflection, direction, orientation, and combinations thereof. FIG. 5 shows an exemplary computing device for implementing the embodiments of the controller 14. In embodiments, the controller 14 includes at least one processing unit 32 and memory 34, which may be volatile (e.g., random access memory "RAM"), non-volatile (e.g., read only memory "ROM," flash memory, etc.), or combinations thereof.

Additionally, the controller 14 may also include additional storage, such as removable storage 38 and/or storage 40. In embodiments, removable and non-removable storage 38 and 40 may include volatile and non-volatile (e.g., non-transitory) storage and may be implemented in any method or technology suitable for storage of information, such as computer readable instructions, data structures, program modules, or other data. In embodiments, memory 34, removable storage 38, and non-removable storage 40 may include, but are not limited to, RAM, ROM, EEPROM, flash memory or other memory technology, compact disks ("CD-ROM"), digital versatile disks ("DVD") or other optical storage, magnetic cassettes, magnetic tape, magnetic disk storage or other magnetic storage devices, or any other medium which can be used to store the desired information and which can be accessed by controller 14. In embodiments, the software for controlling the catheter 12 may be stored on the computer readable media or in memory 34 and/or executed by the processing unit 32.

The controller 14 may also include communications connection(s) 42 that allow for bidirectional or unidirectional communication with other devices, namely, the catheter 12. The communications connection(s) 42 may be embodied as computer readable instructions, data structures, program modules, or other data in a modulated data signal such as a carrier wave or other transport mechanism. The term "modulated data signal" as used herein denotes a signal having one or more of its characteristics set or changed in such a manner as to encode information in the signal. In embodiments, communication media may be transmitted over wired media, such as a wired network or direct-wired connection, and wireless media, such as acoustic, radio frequency, infrared, other wireless media, and combinations thereof.

The computer controller 14 may operate in a networked environment using logical connections to one or more remote computers (not shown). The remote computers may be personal computers, server computer systems, routers, peer devices, network nodes, which may include some or all of the elements described above with respect to the computer controller 14. The logical connections between the computer controller 14 and the remote computer may include a local area network (LAN), a wide area network (WAN), or any other suitable network.

When used in a local area network ("LAN") environment, the computer controller 14 may be connected to the LAN through a network interface or adapter. When used in a wide area network ("WAN") environment, the computer controller 14 may include a modem or other suitable device for establishing communications over the WAN, such as the Internet. The modem, which may be internal or external, may be connected to the computer processor 32 via communication connections 42, or other appropriate mechanism. In a networked environment, program modules or portions thereof may be stored in the remote memory storage device. In embodiments, a remote application programs may reside on a memory device connected to the remote computer system. It will be appreciated that the network connections described are exemplary and other means of establishing a communications link between the computers may be used.

The controller 14 may also include one or more input device(s) 44 such as keyboard, mouse, pen, voice control module 46, touch input device, etc. Output device(s) 48 such as a display, speakers, printer, and the like may also be included. The input devices 44 may help form a user interface while the output devices 48 may display or otherwise output the current status of the catheter 12, e.g., visualization of the procedure.

Figure 6:
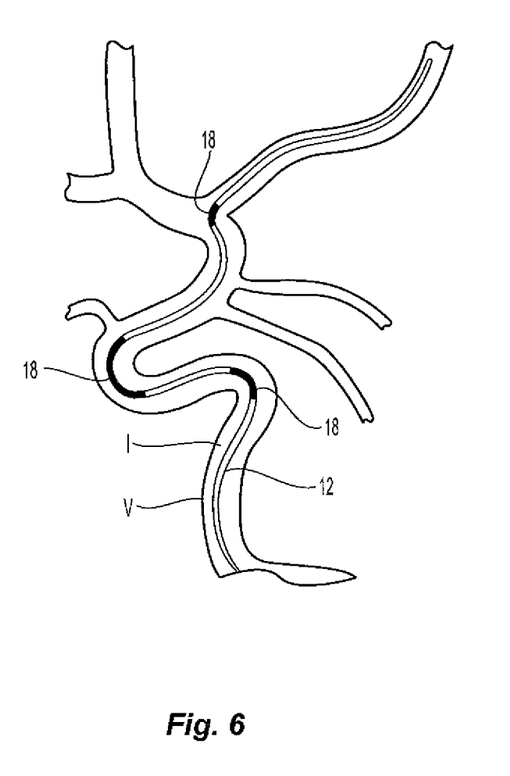
FIG. 6 is a side, cross-sectional view of a vessel with the catheter of FIG. 1 disposed therein in accordance with the principles of the present disclosure.

The output devices 48 may display an internal image of a portion of the body with the catheter 12 disposed therein. In embodiments, the output devices 48 may be coupled to any suitable imaging devices including, but not limited, to X-ray fluoroscopes, CT scanners, and combinations thereof. The images may then be displayed on the output devices 48 to aid the user in guiding the catheter 12 within the lumen "l" of blood vessel "v" as shown in FIG. 6.

The voice control module 46 may include a microphone (not shown) and a speech-recognition engine, which may be embodied in software and/or hardware. In embodiments, the speech-recognition engine may be embodied in the processing unit 32 and/or software executable thereby. The speech-recognition engine digitizes voice commands provided by the user through the microphone. The voice commands are then processed to convert the spoken words into electronic (e.g., digital) form. The digitized commands may be generated by matching the user's speech with commands stored within the controller 14.

The voice control module 46 may perform a grammar process to determine whether the voice commands satisfy certain conditions. The process may include a multiple-branch decision tree in which progress through multiple branching nodes depends on satisfaction of a condition of a previous node. In particular, if the voice command provided by the user satisfies a first condition, then the process proceeds to the first state. If a condition of the current node is satisfied then the process proceeds to the next corresponding state, etc.

In embodiments, voice commands may include a qualifier spoken prior to the actual command to prevent inadvertent actuation of the catheter 12. The qualifier may be a system identifier, such as "robot," "system," "catheter," etc. Therefore when the user provides a voice command, the process initially determines whether the spoken word is the qualifier prior to analyzing the remainder of the voice command. Certain voice commands may not require a qualifier, such as those commands associated with emergency operations, e.g., stopping operation of the catheter 12.

Upon determining that the voice command is proper, namely, whether the command includes a qualifier, the voice control module 46 proceeds to the next state, e.g., node, of determining the actual instructions being provided to the controller 14. In particular, the process determines whether the user has spoken a word that satisfies a condition to advance to the subsequent states. These commands include, but are not limited to, "deflect," "advance," "withdraw," "rotate," "pivot," "track," and combinations thereof.

Each of the commands may also include a subsequent identifier further defining the command. In embodiments, the "deflect" command may be followed by an angle and direction of deflection. The "advance" and "withdraw" commands may be followed by the distance that the user desires the catheter 12 to move within the blood vessel. The "rotate" and "pivot" commands may be followed by a direction of the desired movement. The "track" command may be used to automatically move the catheter 12 in response to tracking movement of another instrument disposed within the blood vessel "v" or tracking of a users head, eyes, hands, or another part of the body, such that if the user looks or motions in a desired direction of the image displayed by the output devices 48, the catheter 12 is moved in the same direction.

In embodiments, the voice control module 46 may be also configured to recognize commands associated with specific anatomical structures. These commands, when interpreted by the controller 14, signal the catheter 12 to conform to the named anatomical structure. The anatomical commands include, but are not limited to, specific blood vessel configurations, neurovascular formations, and the like. Also, the commands may be specific to various malformations including, but, not limited to aneurysms and other arteriovenous malformations (AVMs).

After parsing of the voice commands, the digitized commands from the voice control module 46 are then provided to the processing unit 32, which compares a word, or a combination of words to predefined commands that are stored within a library in the memory 34 of the controller 14. If a word, or combination of words match a word or combination of words in the library, the processing unit 32 provides output commands to a steering control module 50 coupled via the connection 42 to adjust the configuration of the catheter 12 in accordance with the command. In particular, the steering control module 50 receives the output command from the controller 14 and generates one or more control signals corresponding to the output command that result in the adjustment of the EAP actuators 18 to conform the catheter 12 to the desired configuration indicated by the voice command.

With respect to the anatomical structure commands, digital version of the command is also provided to the processing unit 32, which parses the command to determine the configuration of the catheter 12 that conforms to the desired anatomical structure. In particular, the processing unit 32 determines the deflection, direction, pivoting, and any other configuration of the catheter 12 that conforms to the anatomical structure. The processing unit 32 also determines the control signals corresponding to the output command that result in the adjustment of the EAP actuators 18 to conform the catheter 12 to the anatomical structure.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. For example, the principles may be applicable to intravascular guidewires. Thus, it is intended that the present disclosure cover the modifications and variations of this disclosure provided they come within the scope of the appended claims and their equivalents.

What is claimed is:

1. A catheter system comprising:
    a catheter including an elongated flexible body and at least one electroactive polymer actuator disposed along the elongated flexible body, the at least one electroactive polymer actuator adapted to cause a change in configuration of the elongated flexible body; and
    a controller adapted to transmit a control signal to the at least one electroactive polymer actuator, the controller including:
        a memory storing a plurality of control signals corresponding to a plurality of predetermined configurations of the catheter; and
        a user-interface coupled to the memory and configured to receive user input selecting an anatomical structure type from a plurality of predetermined anatomical structure types stored in the memory,
        wherein the controller is configured to select at least one configuration from the plurality of predetermined configurations based on the user input selecting the anatomical structure type from the plurality of predetermined anatomical structure types.

2. The catheter system according to claim 1, wherein the user-interface includes a voice control module.

3. The catheter system according to claim 2, wherein the voice control module includes a microphone and a speech-recognition engine.

4. The catheter system according to claim 3, wherein the speech-recognition engine is configured to detect voice input and to match the voice input to at least one command associated with the at least one configuration, the user input selecting the anatomical structure type from the plurality of predetermined anatomical structure types comprising the voice input.

5. The catheter system according to claim 4, wherein the at least one command is associated with a change in the configuration of the elongated flexible body and is selected from a group consisting of at least one of a blood vessel configuration, a neurovascular formation, or an anatomical malformation.

6. The catheter system according to claim 4, wherein the at least one command corresponds to the anatomical structure type and the at least one configuration corresponds to a shape of the catheter for conforming to an anatomical structure of the anatomical structure type.

7. The system of claim 1, wherein the controller further comprises a processing unit, and wherein the user interface is configured to determine a command based on the user input and the processing unit is configured to receive the command and select the at least one configuration based on the command.

8. The system of claim 1, further comprising a steering control module, wherein the controller is configured to select the at least one configuration by at least causing the steering control module to generate one or more control signals that results in adjustment of the at least one electroactive polymer actuator to conform the catheter to the selected at least one configuration.

9. The system of claim 1, wherein the at least one configuration is selected to conform the catheter to an anatomical structure of the anatomical structure type in response to the at least one command.

10. The system according to claim 1, wherein the anatomical structure type comprises at least one of: a blood vessel configuration type, a neurovascular formation type, or an anatomical malformation type.

11. A method for controlling a catheter for accessing a body lumen, the method comprising:
   receiving, by a controller, a user input selecting an anatomical structure type from a plurality of predetermined anatomical structure types stored in a memory, wherein the catheter includes an elongated flexible body and at least one electroactive polymer actuator disposed along the elongated flexible body, the at least one electroactive polymer actuator adapted to cause a change in configuration of the elongated flexible body;
   selecting, by the controller, at least one configuration for the catheter from a plurality of predetermined configurations based on the user input selecting the anatomical structure type from the plurality of predetermined anatomical structure types; and
   transmitting, by the controller, a control signal to the at least one electroactive polymer actuator to cause a change in configuration of the elongated flexible body to the at least one configuration,
   wherein the controller includes:
      the memory storing a plurality of control signals corresponding to the plurality of predetermined configurations of the catheter; and
      a user-interface coupled to the memory and configured to receive the user input selecting the anatomical structure type from the plurality of predetermined anatomical structure types stored in the memory.

12. The method according to claim 11, wherein receiving the user input includes receiving a voice input.

13. The method according to claim 12, wherein selecting the at least one configuration for the catheter comprises matching the voice input to at least one command associated with the at least one configuration.

14. The method according to claim 13, wherein the at least one configuration is selected to conform the catheter to an anatomical structure of the anatomical structure type in response to the at least one command.

15. The method according to claim 11, wherein the anatomical structure type comprises at least one of: a blood vessel configuration type, a neurovascular formation type, or an anatomical malformation type.

16. A system comprising:
   a catheter including an elongated flexible body and at least one electroactive polymer actuator disposed along the elongated flexible body, the at least one electroactive polymer actuator adapted to cause a change in configuration of the elongated flexible body;
   a computer processor that is operable to execute a computer program product tangibly embodied in a computer-readable storage medium, the computer program product being operable to cause the computer processor to:
      receive a user input for controlling the catheter, wherein the user input selects an anatomical structure type from a plurality of predetermined anatomical structure types stored in a memory;
      select at least one configuration for the catheter from a plurality of predetermined configurations based on the user input selecting the anatomical structure type from the plurality of predetermined anatomical structure types; and
      transmit a control signal to the at least one electroactive polymer actuator to cause a change in configuration of the elongated flexible body to the at least one configuration;
   the memory storing a plurality of control signals corresponding to the plurality of predetermined configurations of the catheter; and
   a user-interface coupled to the memory and configured to receive the user input selecting the anatomical structure type from the plurality of predetermined anatomical structure types stored in the memory.

17. The system according to claim 16, further including:
   a memory coupled to the computer processor storing a plurality of control signals corresponding to the plurality of predetermined configurations of the catheter; and
   a user-interface coupled to the memory, the user-interface configured to receive the user input.

18. The system according to claim 12, wherein the user-interface includes a voice control module.

19. The system according to claim 18, wherein the voice control module includes a microphone and a speech-recognition engine.

20. The system according to claim 19, wherein the speech-recognition engine is configured to detect voice input and to match the voice input to at least one command associated with the at least one configuration, the user input selecting the anatomical structure type from the plurality of predetermined anatomical structure types comprising the voice input.

21. The system according to claim 20, wherein the at least one configuration is selected to conform the catheter to an anatomical structure of the anatomical structure type in response to the at least one command.

22. The system according to claim 16, wherein the anatomical structure type comprises at least one of: a blood vessel configuration type, a neurovascular formation type, or an anatomical malformation type.

* * * * *